United States Patent [19]
Kirschbaum et al.

[11] Patent Number: 5,805,271
[45] Date of Patent: Sep. 8, 1998

[54] REFRACTIVELY CORRECTED, WAVELENGTH SELECTIVE, TRANSPARENT OCCLUDER FOR A NON-TESTED EYE FOR VISUAL FIELD TESTING

[75] Inventors: Alan R. Kirschbaum, Oakland; Christopher L. Petersen, Danville, both of Calif.

[73] Assignee: Carl Zeiss, Inc., Thornwood, N.Y.

[21] Appl. No.: 736,398

[22] Filed: Oct. 24, 1996

[51] Int. Cl.$^6$ ........................................................ A61B 3/02
[52] U.S. Cl. ............................................ 351/224; 351/226
[58] Field of Search .................................... 351/222, 224, 351/226, 227, 230, 246

[56] References Cited

U.S. PATENT DOCUMENTS

| | | | |
|---|---|---|---|
| 2,835,162 | 5/1958 | Harrington et al. | 351/224 |
| 5,220,361 | 6/1993 | Lehmer et al. | 351/224 |
| 5,461,436 | 10/1995 | Campbell | 351/242 |

*Primary Examiner*—Huy Mai
*Attorney, Agent, or Firm*—Michael B. Einschlag

[57] ABSTRACT

An embodiment of the present invention is a refractively corrected, wavelength selective, transparent visual field test occluder for a non-tested eye used in a visual field testing apparatus which uses a stimulus that produces light in a first color spectral range and a background illumination that produces light in a second color spectral range, the visual field test occluder comprising: (a) a base; (b) a fastener configured to fasten the base over a subject's eye; (c) a mounting affixed to the base configured to hold a filter and a refractive lens; and (d) a filter held in the mounting; wherein the filter substantially prevents transmission of light in the first color spectral range and substantially transmits light in the second color spectral range.

9 Claims, 2 Drawing Sheets

REFRACTIVELY CORRECTED, WAVELENGTH SELECTIVE, TRANSPARENT OCCLUDER FOR A NON-TESTED EYE FOR VISUAL FIELD TESTING

TECHNICAL FIELD OF THE INVENTION

The present invention relates to method and apparatus for testing the sensitivity of a subject's visual field. In particular, the present invention is method and apparatus for testing the peripheral vision of a tested eye while preventing retinal rivalry with a non-tested eye.

BACKGROUND OF THE INVENTION

To test the sensitivity of a subject's visual field, it is common practice to use an automated device referred to as a perimeter which surveys the sensitivity of the retina of a tested eye. A typical prior art perimeter projects a variable intensity spot of light, referred to as a stimulus, against a uniformly and constantly illuminated background, for example, a hemispherical projection screen. During the test, the subject views the hemispherical projection screen, typically from the center of a sphere, and directs his/her gaze towards a fixation object, for example, a point source of light or a small black dot that is typically mounted on the surface of the screen. The location of the stimulus is changed in a controlled fashion from one location to another on the hemispherical projection screen to provide a predetermined pattern of points that are spaced apart from the location of the fixation object. The intensity of the stimulus, and the length of time of the stimulus is presented, varies from presentation to presentation in a controlled fashion. In response to the presentation, the subject indicates whether the stimulus is seen at each location, and at each intensity, by depressing a response button if the stimulus is seen. In a typical perimeter presentation of the stimulus, as to location, duration and intensity, is controlled by a computer and the signals produced by the subject's depressing the response button is also detected by the computer. As a result, the sensitivity of the subject's retina is measured and mapped by positioning the point of projection of the stimulus at known locations on the hemispherical projection screen and by changing the duration and intensity of the stimulus. Lastly, only one eye is tested at a time. Hence, during the test, the non-tested eye is typically covered with an opaque or transparent occluder so that only the tested eye is able to see the stimulus. Further, it is frequently necessary to place a lens in front of the tested eye to provide sufficient refractive correction to enable the subject to fixate comfortably on the fixation object.

It is known to occlude the non-tested eye in "white light" visual field testing to ensure that the subject only responds to light entering the tested eye. For example, one prior art occluder used in "white light" visual field testing is a white light translucent patch. Such a white light translucent patch provides background illumination to the non-tested eye that is similar to background illumination seen by the tested eye, however, the white light translucent patch destroys contrast to the extent that the non-tested eye cannot detect the stimulus. Such an occluder was thought to prevent a phenomenon known as retinal rivalry where a visual response from a non-tested eye interferes with a visual response from a tested eye. Retinal rivalry occurs most often whenever the non-tested eye is completely obscured and transmits a "black field" to the brain. In such a case, while the subject is trying to see the stimulus, the tested eye is perceived to become periodically dark or completely black, i.e., it is as if the subject sees nothing. Retinal rivalry is particularly pronounced where a subject has a so-called "dominant eye" where one eye undertakes the transmission of most of the subject's visual information to the brain. Translucent occluders utilized in "white light" visual field testing do not prevent retinal rivalry since typical prior art "white light" visual field testing uses relatively brilliant stimuli. In this case, whenever the field of vision of the tested eye is either at or below threshold for a tested position, it is possible for the non-tested eye to respond to the relatively bright light source passing through the diffuse eye occluder. This produces confusion, i.e., whether the response is due to light seen by the tested eye or to a "flash" seen by the non-tested eye through the white light translucent occluder.

The problem involved in "white light" visual field testing was addressed in U.S. Pat. No. 5,461,436 (the '436 patent). The '436 patent discloses method and apparatus for testing the sensitivity of a subject's visual field wherein the stimulus and the background are different colors, for example, the stimulus is blue and the background is yellow. As is disclosed in the '436 patent, output of the blue stimulus is chosen to be within a narrow spectral range that does not overlap with the spectral range of the yellow background. In order to reduce retinal rivalry, the '436 patent discloses the use of a translucent occluder that is wavelength-sensitive, i.e., it transmits the yellow light of the background but does not transmit the blue light of the stimulus. As a result, both the tested eye and the non-tested eye can see the same yellow background, but only the tested eye can see the stimulus.

A problem exists with the above-described occluder disclosed in the '436 patent in that the subject becomes confused since each eye sees something different. As a result, the subject becomes fatigued and has difficulty maintaining fixation.

In light of the above, there is a need for a method and apparatus for use in testing a subject's visual field that: (a) prevents retinal rivalry and subject fatigue and (b) enables the subject to more easily maintain fixation.

SUMMARY OF THE INVENTION

Embodiments of the present invention advantageously solve the above-identified problem in the prior art and provide method and apparatus for testing a subject's visual field that: (a) prevents retinal rivalry and subject fatigue and (b) enables the subject to more easily maintain fixation. Embodiments of the present invention provide an occluder that prevents retinal rivalry during blue-yellow visual field testing while preventing subject fatigue by enabling the subject to fixate normally using both eyes.

In particular, an embodiment of the present invention is a refractively corrected, wavelength selective, transparent visual field test occluder for a non-tested eye used in a visual field testing apparatus which uses a stimulus that produces light in a first color spectral range and a background illumination that produces light in a second color spectral range, the visual field test occluder comprising: (a) a base; (b) a fastener configured to fasten the base over a subject's eye; (c) a mounting affixed to the base configured to hold a filter and a refractive lens; and (d) a filter held in the mounting; wherein the filter substantially prevents transmission of light in the first color spectral range and substantially transmits light in the second color spectral range.

BRIEF DESCRIPTION OF THE FIGURE

Components which are the same in the various figures have been designated by the same numerals for ease of understanding.

DETAILED DESCRIPTION

Figure 1:
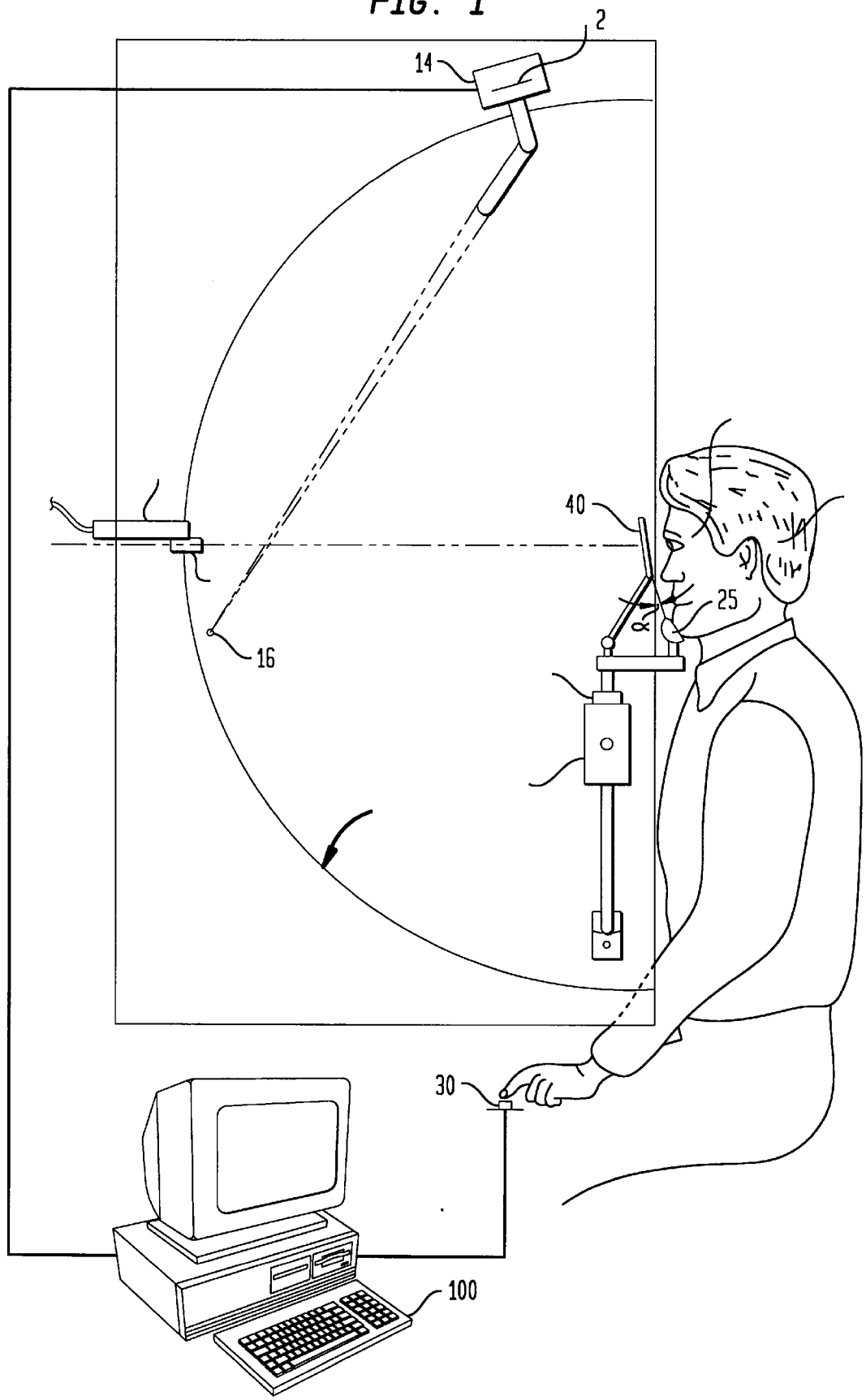
FIG. 1 is a side elevation section of a visual field tester showing a subject undergoing a visual field test.
Figure 2:
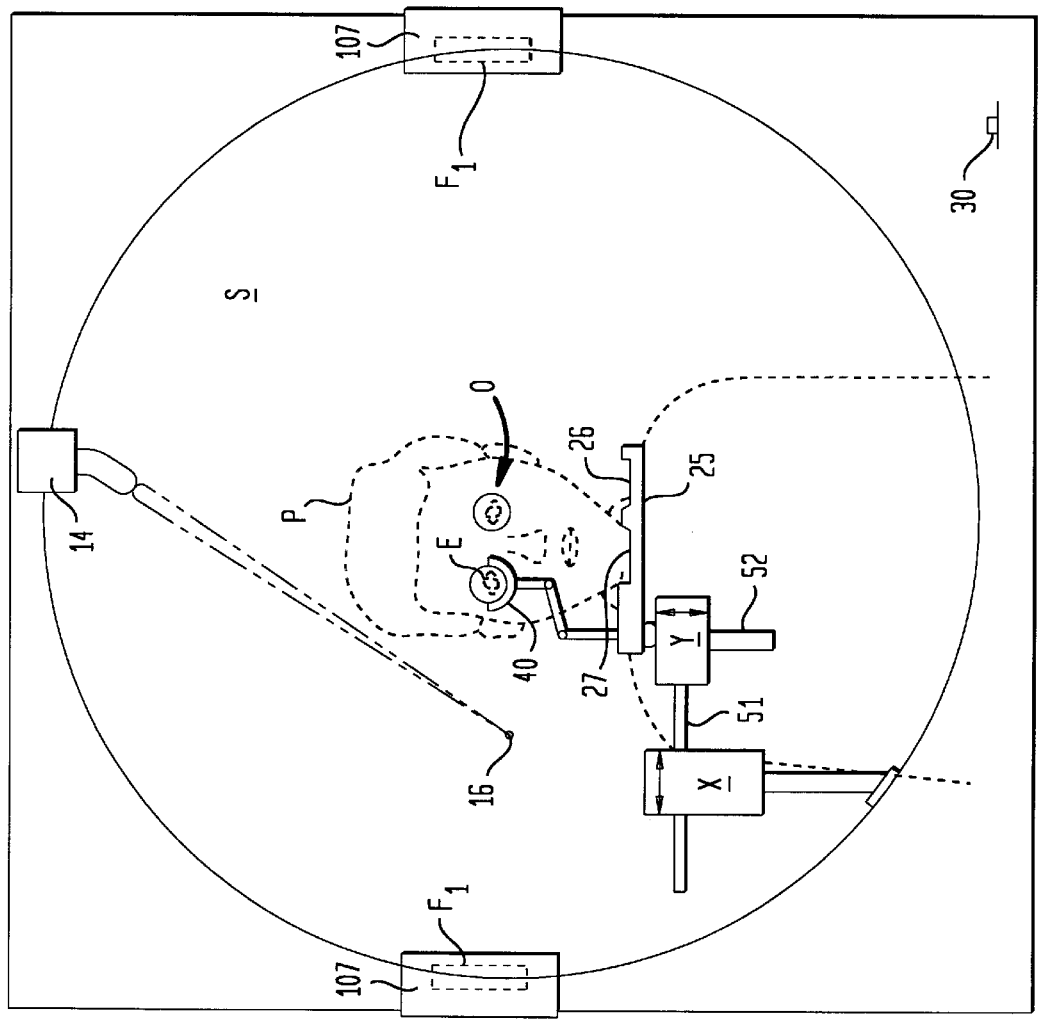
FIG. 2 is a rear elevation section of the subject and visual field tester shown in FIG. 1.

FIGS. 1 and 2 show a side elevation section and a rear elevation section, respectively, of a visual field tester fabricated in accordance with the present invention along with a subject undergoing a visual field test.

As shown in FIG. 1, subject P rests his chin in chin strap 25 and observes hemispherical projection screen S, also referred to as a background field, through refractive correction lens 40 using his left eye E. During the visual field test, subject P fixates on fixation light L disposed at the center of hemispherical projection screen S.

As is shown in FIG. 2, chin rest 25 has two indentations, indentation 26 for testing the subject's right eye and indentation 27 for testing the subject's left eye. As is further shown in FIG. 2, arms 51 and 52 adjust so that chin rest 25 may be placed in different positions to accommodate different subjects. As is still further shown in FIG. 2, background illumination for the visual field tester is provided by light sources 107. In this embodiment, the background illumination is quite bright, being set at between 100 cd/m$^2$ and 200 cd$^2$. In addition, the blue end of the background illumination spectrum is removed with 50% transmission cut-off filters F1 set at 530 nanometers. The background illumination, herein referred to as yellow light, strongly excites the middle and long wavelength retinal cone receptors of the eye, but weakly, if at all, excites the short wavelength retinal cone receptors of the eye.

As shown in FIG. 1, projector 14 operates under the control of controller, for example, computer 100, in a manner which is well known by those of ordinary skill in the art to project a stimulus, i.e., spot 16, onto the surface of hemispherical projection screen S. Subject P indicates that spot 16 is seen by depressing response button 30. The response is detected by computer 100 and mapped in a manner which is well known by those of ordinary skill in the art. An example of such a visual field test apparatus can be purchased, for example, from the Humphrey Instruments division of Carl Zeiss, Inc. of San Leandro, Calif. under the designation Field Analyzer Series 600. In this embodiment, the spot 16 subtends 104 minutes of arc (1°44') on the retina. Further, spot 16 is created in a bright blue light that, in the normal eye, is readily visible in normal fields of peripheral vision. The blue light is provided by placing a narrow-band, dichroic filter F2 which is centered at 440 nanometers in the projection path. The stimulus, herein called blue, strongly excites the short wavelength retinal cone receptors of the eye, but weakly excites the middle and long wavelength retinal cone receptors of the eye.

Figure 3:
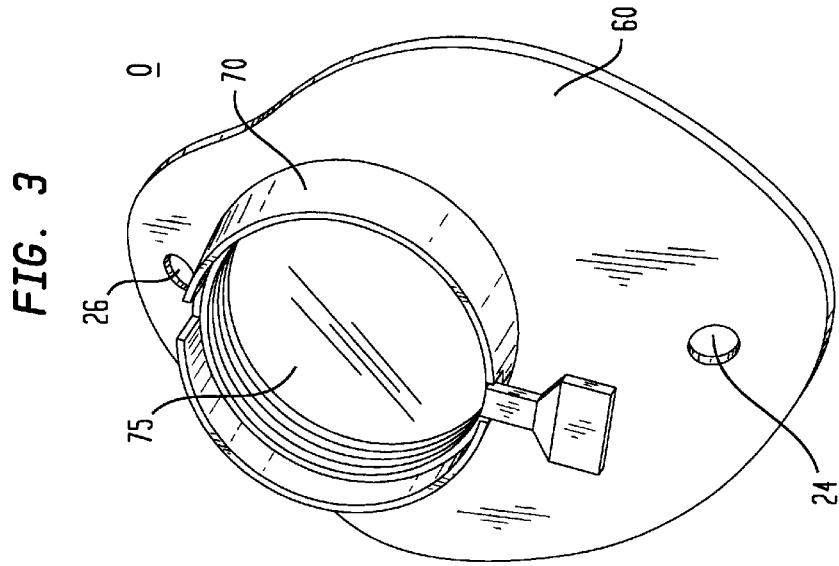
FIG. 3 is perspective view of a visual field test occluder which is fabricated in accordance with the present invention.

FIG. 2 shows eye occluder O in position during the visual field test and FIG. 3 shows a perspective view of occluder O which is fabricated in accordance with the present invention. As shown in FIG. 3, occluder O is a transparent occluder that includes base 60 which is padded with, for example, a plastic foam sealing strip, on the side of the base that will directly abut the skin. The padding enables occluder O to be placed comfortably over the non-tested eye of subject P while excluding extraneous light. Holes 24 and 26 in base 60 are for use with, for example, bands (not shown) for fastening occluder O to the head of subject P. An aperture is provided in base 60, for example, a circular aperture, through which subject P can see. Base 60 of occluder O holds mounting 70 which holds a filter (not shown) and corrective lens 75. The filter, for example, a yellow filter, transmits light in the spectrum of the background illumination but substantially excludes light in the spectrum of the stimulus. For this embodiment, the filter excludes light having a wavelength less than 530 nm. It is preferred that the transmission efficiency of light with wavelengths longer than 530 nm be large. For ease of operation, although not required, it is preferred that the filter be permanently fixed in mounting 75. Mounting 70 is fabricated in accordance with methods which are well known to those of ordinary skill in the art to temporarily hold a lens over the filter, the lens providing refractive correction of the non-tested eye. As a result, and in accordance with this embodiment of the present invention, whenever subject P wears occluder O over the non-tested eye, both the tested eye and the non-tested eye will see the same yellow background and both eyes will see the fixation object clearly. However, only the tested eye will be able to see the blue stimulus. Thus, in accordance with the present invention, because the subject will be able to see the fixation object clearly with both eyes, retinal rivalry is reduced, fatigue is reduced, and the subject is better able to maintain fixation.

Those skilled in the art will recognize that the foregoing description has been presented for the sake of illustration and description only. As such, it is not intended to be exhaustive or to limit the invention to the precise form disclosed. For example, it is not required that the background screen be hemispherical or that the means for indicating a response be a button. Any one of a number of suitable alternatives exist such as, for example, keyboards and the like. Further, it is not required that the occluder be fastened to the head by use of bands. For example, the mounting may be affixed to a head fixture which holds the mounting to cover the non-tested eye.

What is claimed is:

1. A transparent visual field test occluder for a non-tested eye used in a visual field testing apparatus having a stimulus that produces light in a first color spectral range and a background illumination that produces light in a second color spectral range, the transparent visual field test occluder comprising:

a base;

a fastener configured to fasten the base over a subject's eye;

a mounting affixed to the base configured to hold a filter and a refractive lens; and a filter held in the mounting;

wherein the filter substantially prevents transmission of light in the first color spectral range and substantially transmits light in the second color spectral range.

2. The occluder of claim 1 which further comprises a refractive lens held in the mounting.

3. A transparent visual field test occluder for a non-tested eye used in a visual field testing apparatus having a stimulus that produces light in a first color spectral range and a background illumination that produces light in a second color spectral range, the transparent visual field test occluder comprising:

mounting means for positioning a filter and a refractive lens over a subject's eye so that all light received by the eye passes through the filter and the lens; and a filter that substantially prevents transmission of light in the first color spectral range and substantially transmits light in the second color spectral range.

4. The occluder of claim 3 further comprising a refractive lens and fastening means for fastening the mounting means over the subject's eye.

5. A visual field tester for a subject having a tested eye and a non-tested eye which comprises:

a background field;

a fixation object disposed on the background field;

a background light source and a background field illuminator system which projects light from the background light source onto the background field;

a stimulus light source and a stimulus light source system which projects light from the stimulus light source onto the background field at various positions and at various intensities in response to input from a controller;

a response recorder system which receives input from the subject indicating perception of the light projected from the stimulus light source by the tested eye and transmits a signal to the controller; and a transparent occluder which: (a) substantially prevents transmission of light projected from the stimulus light source to the non-tested eye, (b) substantially transmits light projected from the background light source to the non-tested eye; and (c) provides refractive correction for the non-tested eye.

6. The visual field tester of claim 5 wherein the light from the stimulus light source strongly excites the short wavelength retinal cone receptors but weakly excites the middle and long wavelength cone receptors and the light from the background light source strongly excites the middle and long wavelength retinal cone receptors but weakly, if at all, excites the short wavelength cone receptors.

7. The visual field tester of claim 6 wherein the light from the stimulus light source has wavelengths less than 530 nm and the light from the background light source has wavelengths greater than 530 nm.

8. A method of field testing the visual field of a human eye which comprises the steps of:

providing a fixation target for a tested eye and for a non-tested eye;

providing a light stimulus in a first color;

providing a background illumination in a second color, different from the first color; and occluding the non-tested eye in the first color, transparently transmitting light in the second color, and refractively correcting the vision of the non-tested eye.

9. The method of claim 8 wherein the first color is blue and the second color is yellow.

* * * * *